United States Patent [19]

Irikura et al.

[11] 4,429,127

[45] Jan. 31, 1984

[54] QUINOLINE CARBOXYLIC ACID DERIVATIVE

[75] Inventors: Tsutomu Irikura, Tokyo; Hiroshi Koga, Oomiya; Akira Ito, Kuki, all of Japan

[73] Assignee: Kyorin Pharmaceutical Co., Ltd., Tokyo, Japan

[21] Appl. No.: 349,660

[22] Filed: Feb. 17, 1982

[30] Foreign Application Priority Data

Mar. 6, 1981 [JP] Japan ................................. 56-32274

[51] Int. Cl.³ .................. C07D 401/04; A61K 31/495
[52] U.S. Cl. .................................. 544/363; 544/402; 546/156; 424/250
[58] Field of Search ........................................ 544/363

[56] References Cited

U.S. PATENT DOCUMENTS 4,125,615 11/1978 Matsumoto .......................... 424/251
4,292,317 9/1981 Pesson ................................. 546/156
4,327,101 4/1982 Mushika et al. ..................... 546/156

OTHER PUBLICATIONS

Morrison, et al., *Organic Chemistry*, Sec. Ed., 1966, Allyn and Bacon, Inc., Boston, pp. 466–467 and 730–735.

*Primary Examiner*—Donald G. Daus
*Assistant Examiner*—James H. Turnipseed
*Attorney, Agent, or Firm*—Armstrong, Nikaido, Marmelstein & Kubovcik

[57] ABSTRACT

This invention relates to a new compound of value as antibacterial agent. More particularly, it relates to a quinoline carboxylic acid derivative and the acid addition salts thereof.

1 Claim, No Drawings

QUINOLINE CARBOXYLIC ACID DERIVATIVE

DETAILED DESCRIPTION OF THE INVENTION

This invention relates to a new and useful quinoline carboxylic acid derivative having a potent antibacterial activity.

Antibacterial agents such as nalidixic acid, piromidic acid and pipemidic acid have been proved highly effective in the therapy of infections due to gram-negative bacteria, but such agents suffer the serious disadvantage of having only weak activities against most gram-positive bacteria. The compound of the present invention is particularly useful in that it possesses potent antibacterial activities against both gram-positive and gram-negative bacteria.

The new compound of the present invention is a quinoline carboxylic acid derivative having the formula (I)

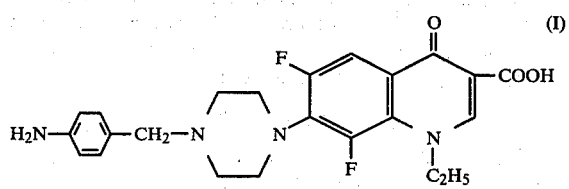

and the pharmaceutically acceptable salts thereof. The compound (I) is highly effective in the therapy of infections due to gram-positive and gram-negative bacteria and it has been found that the compound (I) is fortunately metabolized in part to 1-ethyl-6,8-difluoro-1,4-dihydro-4-oxo-7-(1-piperazinyl)quinoline-3-carboxylic acid having superior activity against gram-negative bacteria when administered to animals.

The compound (I) can be prepared by the reduction of a compound of the formula (II)

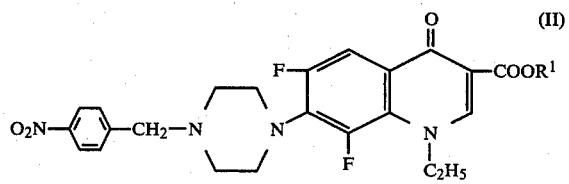

wherein $R^1$ is hydrogen or lower alkyl group, if necessary, followed by hydrolysis by the usual method. The reduction was accomplished by catalytic hydrogenation using palladium on charcoal, Ranney-nickel, platinum oxide, or the like as catalyst in an inert solvent such as, for example, alcohols, ethers, or organic acids, or by the reaction with metal such as, for example, iron, tin or zink, or the halide or the sulfate in the presence of acid such as, for example, hydrochloric acid, sulfuric acid, or acetic acid.

Also, the compound (I) was obtained by the amination of a compound of the formula (III),

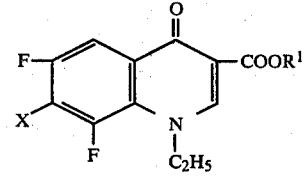

wherein $R^1$ is the same as mentioned above and X is a releasing group such as halogen or sulfonyloxy group, with a piperazine derivative of the formula (IV),

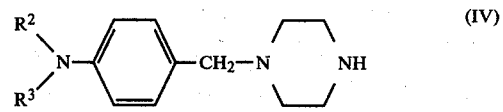

wherein $R^2$ and $R^3$ are hydrogen or protecting group such as acyl group, in an inert solvent such as, for example, water, alcohols, ethers, amines, nitriles, dimethylformamide or dimethylsulfoxide, preferably in the presence of an organic or inorganic base, at a temperature in the range of room temperature to 170° C., if desired, followed by hydrolysis with acids or alkalis by the usual method.

Starting material (II) was obtained by the reaction of a compound (III) with N-(p-nitrobenzyl)piperazine or by the treatment of a compound of the formula (V),

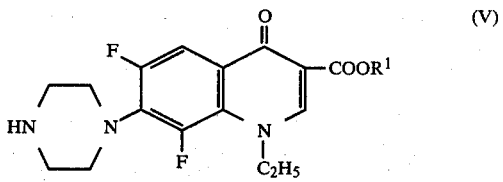

wherein $R^1$ is the same as mentioned above, with a compound of the formula (VI),

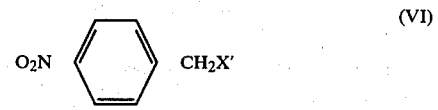

wherein X' is halogen,

The salts such as, for example, methanesulfonate, benzenesulfonate, acetate, maleate, citrate, malate, lactate, hydrochloride, sulfate, phosphate, sodium salt, potassium salt and amine salts, or the like, of the compound (I) are obtained by the usual manner.

The compound (I) or the salt is administered to human or animals, generally in the range of 1–100 mg/kg/day by an oral or parenteral route. The compound (I) or the salt may be used in the form of pharmaceutical preparations such as, for example, tablets, capsules, sirups, injections, granules, powder, suppositories, or emulsions. The pharmaceutical preparations may contain the compound in admixture with an adjuvant and are formed by conventional methods.

The following examples serve to illustrate the invention.

EXAMPLE 1

A mixture of 1-ethyl-6,8-difluoro-1,4-dihydro-4-oxo-7-(1-piperazinyl)quinoline-3-carboxylic acid hydrochloride (6.7 g), triethylamine (5.45 g), p-nitrobenzylbromide (5.8 g) and dimethylformamide (200 ml) was stirred at 90° C. for 10.5 hrs. The solvent was evaporated off and the residue was treated with water. The solid was filtered, washed with water, dried, and recrystallized from a mixture of dimethylformamide and ethanol to give 6.9 g of 1-ethyl-6,8-difluoro-1,4-dihydro-7-[4-(p-nitrobenzyl)-1-piperazinyl]-4-oxoquinoline-3-carboxylic acid. mp: 241°–242° C.

|  | C | H | N |
|---|---|---|---|
| Anal. Calcd. for $C_{23}H_{22}F_2N_4O_5$ | 58.47 | 4.69 | 11.86 |
| Found | 58.50 | 4.59 | 11.95 |

EXAMPLE 2

A mixture of 1-ethyl-6,8-difluoro-1,4-dihydro-7-[4-(p-nitrobenzyl)-1-piperazinyl]-4-oxoquinoline-3-carboxylic acid (6.0 g), acetic acid (150 ml), and 5% palladium on charcoal (1.0 g) was hydrogenated. The slurry was filtered and the filtrate concentrated to dryness. The residue was treated with water, neutralized with aqueous sodium hydroxide solution and extracted with dichloromethane. The organic layer was dried and evaporated. The residue was chromatographed on silica gel. Elution with a mixture of chloroform and ethanol (20:1) and recrystallization from a mixture of chloroform and ethanol gave 7-[4-(p-aminobenzyl)-1-piperazinyl]-1-ethyl-6,8-difluoro-1,4-dihydro-4-oxoquinoline-3-carboxylic acid.
mp: 220°–221° C.

|  | C | H | N |
|---|---|---|---|
| Anal. Calcd. for $C_{23}H_{24}F_2N_4O_3$ | 62.43 | 5.47 | 12.66 |
| Found | 62.53 | 5.36 | 12.68 |

EXPERIMENT 1

Antibacterial activity (in vitro)

The minimum inhibitory concentration (MIC) of the compound (I) was determined by an agar dilution technique (the standard method of Japan Society of Chemotherapy) against standard strains of gram-positive and gram-negative bacteria.

As shown in Table 1, nalidixic acid and pipemidic acid exerted antibacterial activity mainly on gram-negative bacteria, and were inactive on many strains of gram-positive bacteria.

On the other hand, the compound (I) was more active than nalidixic acid and pipemidic acid against both of gram-positive and gram-negative bacteria. Expecially the antibacterial activity of the compound (I) was more potent against gram-positive bacteria containing Streptococcus spp. which were not susceptible to nalidixic acid and pipemidic acid.

EXPERIMENT 2

Antibacterial activity (in vivo)

The in vivo antibacterial activity of the compound (I) was determined in systemic infection in mice. The systemic infections were produced in male mice ICR (body weight, 19±2 g) by inoculating intraperitoneally with Staphylococcus aureus Smith and E. coli ML4707. The compounds were administered orally in divided doses at 0 and 4 hrs. after infection. The therapeutic effect of drugs was judged from the number of mice surviving after 7 days of observation. A comparison of in vivo antibacterial activity was made on the basis of the mean effective dose ($ED_{50}$) calculated by the method of Litchfield and Wilcoxon.

As shown in Table 2, the in vivo antibacterial activity of the compound (I) was significantly more effective than that of nalidixic acid and pipemidic acid against S. sureus Smith. The potency of the compound (I) was superior 172 times than that of nalidixic acid, and 62 times than that of pipemidic acid.

EXPERIMENT 3

Tissue levels of the compound (I) after a single oral administration of 50 mg/kg in mice and rats Tissue levels of the compound (I) were determined by micro-biological assay which employed the thin layer cup method with Bacillus subtilis ATCC6633 as the test organism. Serum and tissue levels of the compound (I) were calculated with the standard curve prepared in normal serum of the test animal species and M/15 phosphate buffer (pH 7.5), respectively. The results were shown in Table 3. After the single oral administration of 50 mg/kg of the compound (I) in mice and rats, a peak serum level was reached at 8.6 and 5.3 μg/ml, respectively, within 30–60 minutes. The level of the compound (I) in lung, liver and kidney were higher than those in serum with both species. The transferability of the compound (I) in tissues was very excellent.

EXPERIMENT 4

Acute toxicity of the compound (I)

Acute toxicity of the compound (I) was examined in mice (ICR strain, 7 weeks old). Observation period was 7 days after a single oral and intravenous administration.

As shown in Table 4, the compound (I) has a low toxicity.

TABLE 1

In vitro antibacterial activity of the present compound

| Organism | Gram | MIC (μg/ml) Present compound | Metabolite* | NA** | PPA*** |
|---|---|---|---|---|---|
| Bacillus subtilis PCI 219 | + | 0.1 | 0.2 | 6.25 | 6.25 |
| Staphylococcus aureus 209P | + | 0.1 | 0.78 | 100 | 25 |
| S. aureus IID670 (Terajima) | + | 0.2 | 0.78 | >100 | 25 |
| S. epidermidis IID866 | + | 0.2 | 0.78 |  |  |
| Streptococcus pyogenes IID692 | + | 0.78 | 3.13 | >100 | >100 |
| S. pyogenes S-8 | + | 0.78 | 12.5 | >100 | >100 |
| S. pneumoniae IID552 | + | 0.39 | 6.25 | >100 | >100 |
| S. faecalis IID682 | + | 0.78 | 3.13 | >100 | >100 |

TABLE 1-continued

In vitro antibacterial activity of the present compound

| Organism | Gram | Present compound | MIC (μg/ml) Metabolite* | NA** | PPA*** |
|---|---|---|---|---|---|
| E. coli NIHJ JC-2 | — | 0.20 | 0.05 | 3.13 | 1.56 |
| E. coli ATCC10536 | — | 0.39 | 0.05 | 3.13 | 1.56 |
| Haemophilus influenzae IID986 | — | 0.20 | 0.025 | 1.56 | 3.13 |
| Klebsiella pneumoniae IFO3512 | — | 0.1 | 0.05 | 1.56 | 1.56 |
| Proteus vulgaris IFO3167 | — | 1.56 | 0.05 | 3.13 | 3.13 |
| P. mirabilis IID994 | — | 1.56 | 0.05 | | |
| P. morganii IID602 | — | 1.56 | 0.1 | | |
| Enterobacter cloacae IID977 | — | 1.56 | 0.1 | | |
| Citrobacter freundii IID976 | — | 1.56 | 0.1 | | |
| Shigella sonnei IID969 | — | 0.39 | 0.05 | 1.56 | 1.56 |
| Salmonella enteritidis IID604 | — | 1.56 | 0.1 | 12.5 | 12.5 |
| Yersinia enterocolitica IID981 | — | 1.56 | 0.1 | | |
| Serratia marcescens IID618 | — | 3.13 | 0.1 | | |
| Pseudomonas aeruginosa V-1 | — | 12.5 | 0.78 | 100 | 12.5 |
| P. aeruginosa IFO12689 | — | 25 | 1.56 | >100 | 25 |
| Acinetobacter enitratus IID876 | — | 0.78 | 0.78 | | |
| Alcaligenes faecalis 0104002 | — | 3.13 | 0.78 | | |

Inoculum size: $10^8$ cells/ml
*1-Ethyl-6,8-difluoro-1,4-dihydro-4-oxo-7-(1-piperazinyl)quinoline-3-carboxylic acid
**Nalidixic acid
***Pipemidic acid

TABLE 2

In vivo antibacterial activity of the present compound

| Strain | Challenge dose (cells/animal) | Compound | MIC (μg/ml) | ED$_{50}$ (mg/kg) |
|---|---|---|---|---|
| Staphylococcus aureus Smith | 2.4 × 10$^5$ (in BHI* containing mucin) | Present compound | 0.05 | 3.7 |
| | | NA** | 25 | 635 |
| | | PPA*** | 12.5 | 231 |
| E. coli ML4707 | 1.2 × 10$^7$ (in saline) | Present compound | 0.39 | 13.8 |
| | | NA** | 3.13 | 38.3 |
| | | PPA*** | 1.56 | 38.9 |

*Brain heart infusion
**Nalidixic acid
***Pipemidic acid

TABLE 3

Tissue levels of the present compound

| Animal | Tissue | Concentration (μg/ml) Time after administration (hour) | | | | |
|---|---|---|---|---|---|---|
| | | 0.5 | 1.0 | 2.0 | 4.0 | 6.0 |
| Mouse | Serum | 8.6 | 6.5 | 5.0 | 2.7 | 1.8 |
| | Lung | 12.8 | 9.5 | 5.5 | 4.3 | 2.8 |
| | Liver | 22.5 | 17.5 | 12.0 | 9.0 | 5.8 |
| | Kidney | 13.0 | 13.0 | 7.8 | 4.6 | 4.6 |
| Rat | Serum | 4.8 | 5.3 | 1.2 | 0.2 | 0.2 |
| | Lung | 6.0 | 8.6 | 2.1 | 0.6 | ND* |
| | Liver | 14.0 | 15.4 | 6.2 | 2.2 | 0.8 |
| | Kidney | 6.6 | 6.8 | 2.7 | 1.0 | 0.3 |

*not detected

TABLE 4

Acute toxicity of the present compound in male mice

| Route of administration | LD$_{50}$ (mg/kg) |
|---|---|
| iv | 250–300 |
| po | >4,000 |

What is claimed is:
1. A compound having the following formula

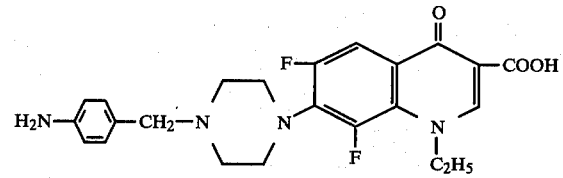

and a pharmaceutically acceptable salt thereof.

* * * * *